(12) United States Patent
Lee et al.

(10) Patent No.: US 10,335,517 B2
(45) Date of Patent: Jul. 2, 2019

(54) POROUS POLYMER MATERIAL, PREPARATION METHOD THEREFOR, AND BIOMATERIAL USING SAME

(71) Applicant: DANKOOK UNIVERSITY CHEONAN CAMPUS INDUSTRY ACADEMIC COOPERATION FOUNDATION, Cheonan-si (KR)

(72) Inventors: Han-a-reum Lee, Seongnam-si (KR); Ho-yong Kim, Incheon (KR); Jin-hyun Park, Cheonan-si (KR); June-ho Byun, Busan (KR); Jin-ho Lee, Daejeon (KR); Se-heang Oh, Cheonan-si (KR)

(73) Assignee: Dankook University Cheonan Campus Industry Academic Cooperation Foundation, Cheonan-Si (KR)

( * ) Notice: Subject to any disclaimer, the term of this patent is extended or adjusted under 35 U.S.C. 154(b) by 0 days.

(21) Appl. No.: 15/547,050

(22) PCT Filed: Sep. 21, 2015

(86) PCT No.: PCT/KR2015/009866
§ 371 (c)(1),
(2) Date: Jul. 27, 2017

(87) PCT Pub. No.: WO2016/122080
PCT Pub. Date: Aug. 4, 2016

(65) Prior Publication Data
US 2018/0043061 A1 Feb. 15, 2018

(30) Foreign Application Priority Data
Jan. 29, 2015 (KR) ........................ 10-2015-0014179

(51) Int. Cl.
| | | |
|---|---|---|
| A61K 9/14 | (2006.01) |
| A61L 27/56 | (2006.01) |
| A61L 27/18 | (2006.01) |
| A61L 27/22 | (2006.01) |
| A61L 27/54 | (2006.01) |
| A61L 31/06 | (2006.01) |
| A61L 31/14 | (2006.01) |
| A61L 31/16 | (2006.01) |

(52) U.S. Cl.
CPC .............. *A61L 27/56* (2013.01); *A61L 27/18* (2013.01); *A61L 27/227* (2013.01); *A61L 27/54* (2013.01); *A61L 31/06* (2013.01); *A61L 31/146* (2013.01); *A61L 31/16* (2013.01); *A61L 2300/414* (2013.01)

(58) Field of Classification Search
None
See application file for complete search history.

(56) References Cited

U.S. PATENT DOCUMENTS 4,873,091 A * 10/1989 Jankower ................... C08J 3/12
424/489
9,029,431 B2 * 5/2015 Nair .......................... C08J 9/283
430/108.1

FOREIGN PATENT DOCUMENTS

| KR | 10-2010-0013016 A | 2/2010 |
|---|---|---|
| KR | 2010-0101637 A | 4/2012 |
| KR | 10-2012-0114797 A | 10/2012 |
| KR | 10-2013-0029291 A | 3/2013 |
| KR | 10-1293209 B1 | 3/2013 |
| KR | 10-2013-0097409 A | 9/2013 |
| KR | 10-2014-0132618 A | 11/2014 |
| KR | 10-2015-0108956 A | 10/2015 |

OTHER PUBLICATIONS

Young Min Shin et al., Current Status of Tissue Engineering Scaffolds Using Biodegradable Polymers (Polymer Science and Technology vol. 18, No. 5, 2007, 458-464).
In Kab Koh et al., Regenerative Medicine and Tissue Engineering: Functionalized Polymeric Scaffolds for in situ Tissue Regeneration (Polymer Science and Technology vol. 22, No. 1, 2011, 17-26).

* cited by examiner

*Primary Examiner* — Susan T Tran
(74) *Attorney, Agent, or Firm* — Patent Office of Dr. Chung Park (57) ABSTRACT

The present invention relates to: a porous polymer material having a porous structure over the entire polymer and having a dense porous structure in which pores are connected to each other therein. The porous polymer material is harmless to the human body as it does not use toxic organic solvents. In addition, a porous polymer material can be prepared without using any additives for forming pores and the particle size can be easily controlled, and thus a polymer material suitable for various uses can be prepared. Furthermore, the extended release of a loaded bioactive material is possible only by the dense porous structure of a polymer itself without using an additive and a surface modification method in the porous polymer material of the present invention. Therefore, the porous polymer material can be applied to a biodegradable material in various bio-fields requiring the extended release of a bioactive material.

7 Claims, 5 Drawing Sheets

POROUS POLYMER MATERIAL, PREPARATION METHOD THEREFOR, AND BIOMATERIAL USING SAME

CROSS-REFERENCE TO PRIOR APPLICATIONS

This application is a national Stage Patent Application of PCT International Patent Application No. PCT/KR2015/009866, filed on Sep. 21, 2015 under 35 U.S.C. § 371, which claims priority of Korean Patent Application No. 10-2015-0014179, filed on Jan. 29, 2015, which are all hereby incorporated by reference in their entirety.

TECHNICAL FIELD

The present invention relates to a porous polymer material, a preparation method therefor, and a biomaterial using the same.

BACKGROUND ART

Although many leading researchers have come up with various definitions of what tissue engineering is, the ultimate goal of the tissue engineering is all the same in that it is a technology which combines bioscience knowledge with engineering knowledge to regenerate damaged organs.

Although many factors should be taken into account for successful tissue regeneration, various approaches have been attempted, depending on physical, biological, and chemical characteristics of desired tissues, focusing on mainly three crucial components.

The first component is cells that constitute the vast majority of tissues. Essentially, the human organs, such as skin, blood vessels, nerves, bones, and mussels, are composed of cells, and because the organs that are subjects of tissue engineering are different in the kind, composition, and function of their constituent cells, it is necessary to fully consider how each cell can be used. Regeneration of function, rather than simply regeneration of form, is the most important goal, and thus cells that are best suited to the tissue to be regenerated should be used.

The second crucial component of the tissue engineering is a biomaterial. As mentioned above, tissue is a system in which a variety of cells are fused to form organisms. Thus, there is an ideal tissue form or cell composition for regenerating specific tissue and a biomaterial acts as a framework for developing organism of fused cells.

In addition, for ideal tissue regeneration, the biomaterial needs to meet various essential properties. The representative properties include (1) biodegradability and non-toxic, (2) interconnected internal porous structure with a large surface area, (3) structural stability, (4) provision of a cellular adsorption, (5) low immunoreactivity, (6) inhibition of thrombus formation, (7) hydrophilicity, and (8) biofunctionality.

Finally, in order to artificially grow tissues, it is necessary to implement a human-like cellular environment that can regulate the physiological activities of cells on the basis of cells and biomaterial.

In a new tissue engineering approach that does not provide cells, the role of bioactive molecules is crucial. The bioactive molecules are an important factor that can control the environment of our body, and they are composed of growth factors or cytokine. The bioactive molecules regulate the migration, proliferation, differentiation and homing of stem cells or progenitor cells present in the body, thereby securing enough stem cell counts in the transplanted biomaterial to induce effective tissue regeneration.

In order to deliver effective bioactive molecules for regeneration of tissues, it is necessary to spatially and temporally controlled release of bioactive molecules with sufficient bioactivity for a long period of time.

However, most of the bioactive molecules are easily degraded by enzymes present in the body or are liable to lose activity, and a bolus injection at a target site may cause cytotoxicity due to a high concentration of bioactive molecules at the time of injection.

For these reasons, the bioactive molecules are locally transferred using a sustained-release delivery method that chemically immobilizes or incorporates the bioactive molecules into a biomaterial and releases the biomaterial slowly while maintaining a specific effective concentration. This delivery method is dependent on the properties of the material, which controls and the release of bioactive molecules according to temperature, pH, electromagnetic field, degree of biodegradation of polymer, and the like.

Conventional methods for sustained release of bioactive molecules include covalent immobilization using surface modification and heparin intermediated immobilization using heparin as an additive.

The covalent immobilization through surface modification is a method of immobilizing growth factors by modifying a surface of the biomaterial with an amine group, hydrolyzing growth factors by use of 1-ethyl-3-(3-dimethylaminopropyl)-1-carbodiimide hydrochloride (EDC)/N-hydroxysuccinimide (NHS) to expose carboxyl groups to the surface, thereby fixing the amine group of the surface of the biomaterial and the carboxyl groups of the growth factors with covalent bonds.

In addition, the heparin intermediated immobilization is a method which is widely used to effectively introduce growth factors into a porous biomaterial, wherein heparin acts as an intermediator which links a polymer surface with the growth factors. Generally, heparin can be introduced from the polymer surface via covalent bonds with amine groups present on the polymer surface, or through hydrogen bonding with O-functional groups existing on the polymer surface, and then, the growth factors may be immobilized on the surface of the biomaterial through ionic bonds between O-sulfate/N-sulfate existing in the heparin and lysine/arginine of the growth factors (See Patent Document 1).

However, it is known that the covalent bonds between the amine groups existing on the surface of the biomaterial and heparin degrades the biological function of heparin, thereby lowering the interaction with the growth factors. In addition, the above two methods are too complicated and have a disadvantage that EDC/NHS exhibits a harmful toxicity to a human body.

Therefore, a biomaterial for tissue regeneration which maintains a bioactivity for a long period of time without using toxic additives for sustained release of bioactive molecules and is harmless to a human body has not yet been developed.

RELATED ART

Patent Document(s)

Patent Document 1: Korean Patent Registration No. 10-1293209
Patent Document 2: Korean Patent Application No. 2010-0101637

Non-Patent Document(s)

Non-Patent Document 1: "Current Status of Tissue Engineering Scaffolds Using Biodegradable Polymers" (Polymer Science and Technology Vol. 18, No. 5, 2007, 458-464)

Non-Patent Document 2: "Regenerative Medicine and Tissue Engineering: Functionalized Polymeric Scaffolds for in situ Tissue Regeneration" (Polymer Science and Technology Vol. 22, No. 1, 2011, 17-26)

Disclosure

Technical Problem

The present invention is directed to solve the problems of conventional biopolymer materials used in tissue engineering and overcome the limitations thereof. An objective of the present invention is to provide a porous polymer material capable of inducing sustained release of bioactive molecules using only a unique structure of polymer itself without using any additives and surface modification methods for loading the bioactive molecules into the polymer material.

In addition, another objective of the present invention is to provide a method of preparing a porous polymer material having the aforementioned characteristics.

Additionally, another objective of the present invention is to provide various biomaterials using the above porous polymer material.

Technical Solution

One aspect of the present invention provides a porous polymer material having a porous structure over the entire polymer and having a dense porous structure in which pores are connected to each other therein.

The porous polymer material may be in the form of particles or in the form of a sheet.

When the porous polymer material is in the form of particles, an average particle size is 10 to 3000 μm.

The porous polymer may be at least one selected from the group consisting of poly(ε-caprolactone), polydioxanone, poly(lactic acid), poly(glycolicacid), a poly(lactic acid-co-glycolic acid) copolymer, a copolymer of poly(β-hydroxybutyrate) and polyhydroxybutyric acid-cohydroxyvalericacid, poly(γ-ethyl glutamate), a polyanhydride copolymer, a polyethylene oxide-polylactic acid copolymer, a polyethyleneoxidepolylactic-co-glycolic acid copolymer, and a polyethylene oxide-polycaprolactone copolymer.

The porous polymer material may further include hydrophilic polymer.

The hydrophilic polymer may be at least one selected from the group consisting of a polyethylene oxide-polypropylene oxide copolymer, a polyethylene oxide-polylactic acid copolymer, a poly(lactic acid-co-glycolic acid) copolymer, a polyethylene oxide-glycolic acid copolymer, a polyethyleneoxidepolylactic-co-glycolic acid copolymer, a polyethylene oxide-polydioxanone copolymer, and copolymers thereof.

Another aspect of the present invention is to provide a biomaterial using a porous polymer material which has a porous structure over a surface and an inside of polymer and has a dense porous structure in which pores are connected to each other inside of the polymer.

Bioactive molecules may be loaded in the porous polymer material and the loaded bioactive molecules may be released from the porous polymer material in a sustained manner.

The bioactive molecules may be loaded in the surface and the inside of the porous polymer material.

A sustained release of the bioactive molecules may be accomplished by repeating desorption/adsorption of the bioactive molecules on the dense porous structure of the polymer material in which the pores are connected to each other while the bioactive molecules loaded in the porous polymer material pass through the dense porous structure.

The bioactive molecule may be at least one selected from: at least one kind of peptide/protein selected from the group consisting of cytokine, hormone, insulin, and antibodies; at least one kind of growth factor selected from the group consisting of fibroblast growth factors (FGFs), a vascular endothelial growth factor (VEGF), a nerve growth factor (NGF), a brain-derived neurotrophic factor (BDNF), transforming growth factors (TGFs), bone morphogenetic proteins (BMPs), an epidermal growth factor (EGF), an insulin-like growth factor (IGF), and a platelet-derived growth factor (PDGF); genes; and vaccines.

The biomaterial may be at least one selected from cosmetic filling materials, filling materials for treatment of urinary incontinence, filling materials for treatment of fecal incontinence, filling materials for reconstruction of vocal cords, bone filling materials, and tissue engineering supports.

Still another aspect of the present invention is to provide a method of preparing a porous polymer material with particle shape, including: precipitating polymer by spraying a polymer solution and a compressed air into a non-solvent; and washing and drying the polymer precipitated in the non-solvent to produce a porous polymer material.

The polymer solution may be sprayed as a spherical form in a droplet state into the non-solvent.

The polymer solution and the compressed gas may be simultaneously sprayed using a double injection nozzle device.

The double injection nozzle device may be positioned at a distance of 1 to 50 cm from the non-solvent.

The compressed gas may be sprayed at a rate of 0.1 to 50 L/min.

Yet another aspect of the present invention is to provide a method of preparing a porous polymer material with sheet shape, including: filling a polymer solution in a mold; and precipitating, washing, and drying polymer filled in the mold.

In each of the above methods, a concentration of the polymer solution may range from 1 to 50% by weight.

In each of the above methods, a solvent used for preparation of the polymer solution may be at least one selected from the group consisting of tetraglycol, 1-methyl-2-Pyrrolidinone (NMP), triacetin, and benzyl alcohol.

In each of the above methods, the polymer may be at least one selected from the group consisting of poly(ε-caprolactone), polydioxanone, poly(lactic acid), poly(glycolicacid), a poly(lactic acid-co-glycolic acid) copolymer, a copolymer of poly(β-hydroxybutyrate) and polyhydroxybutyric acid-cohydroxyvalericacid, poly(γ-ethyl glutamate), a polyanhydride copolymer, a polyethylene oxide-polylactic acid copolymer, a polyethyleneoxidepolylactic-co-glycolic acid copolymer, and a polyethylene oxide-polycaprolactone copolymer.

In each of the above methods, the non-solvent may be at least one selected from the group consisting of water, ethanol, methanol, isopropanol, hexane, and ether.

In each of the above methods, the polymer solution may further include at least one kind of hydrophilic polymer selected from the group consisting of a polyethylene oxide-polypropylene oxide copolymer, a polyethylene oxide-polylactic acid copolymer, a poly(lactic acid-co-glycolic acid) copolymer, a polyethylene oxide-glycolic acid copolymer, a polyethyleneoxidepolylactic-co-glycolic acid copolymer, a polyethylene oxide-polydioxanone copolymer, and copolymers thereof.

The hydrophilic polymer may be contained in an amount of 0.1 to 50% by weight of the total polymer solution.

Advantageous Effects

The porous polymer material according to the present invention has a porous structure over the entire surface and the inside thereof, and particularly, pores inside of the material are connected to each other to have a complex and dense porous structure.

The porous polymer material according to the present invention may allow preparation of a biomaterial harmless to a human body with a simple process without using toxic organic solvents. In addition, the prepared porous polymer material may be used in various forms including particles, sheets, or the like.

According to the preparation method of the present invention, it is possible to prepare a porous material in the form of fine particles and in the form of sheet without using any toxic additive for pore formation, and particles of various sizes may be produced by easily controlling the particle size according to conditions.

In addition, the sustained release of a loaded material is possible only by a unique structure of the polymer material itself without using any additive and surface modification method on the surface of the porous polymer material.

Therefore, the porous polymer material according to the present invention can be applied to a material in various bio-fields requiring the sustained release of bioactive molecules depending on the particle size of the porous polymer material.

MODES OF THE INVENTION

Hereinafter, exemplary examples of the present invention will be described in detail.

The terminology used in the detailed description is provided only to describe examples of the present invention and not for purposes of limitation.

Unless the context clearly indicates otherwise, the singular forms include the plural forms. It will be understood that the terms "comprises" or "includes," when used herein, specify some features, numbers, steps, operations, elements, and/or groups thereof, but do not preclude the presence or possibility of one or more other features, numbers, steps, operations, elements, and/or groups thereof in addition to the description.

The present invention relates to a porous polymer material, a method of preparing the same, and various biomaterials using the same.

The porous polymer material according to the present invention has a porous structure over the entire polymer and has a dense porous structure in which pores are connected to each other.

The term "porous polymer material having a porous structure over the entire polymer," which is used throughout the specification of the present invention, means that a plurality of pores are formed in the structure of the entire polymer material including the surface and inside (cross-section) of the polymer material according to the present invention.

In addition, the term "dense porous structure in which pores are connected to each other," which is used throughout the specification of the present invention, means that the plurality of pores in the porous polymer material are connected to each other while polymers are shaped into, for example, bundles and the bundles connected to each other are densely packed.

Moreover, the term "biomaterial," which is used throughout the specification of the present invention, is meant to include all substances that do not show bio-rejection reaction or toxic reaction upon contact with a living tissue, blood, body liquid, or the like, that is, all materials having biocompatibility as materials developed as a means for a human implant material and for diagnosing and treating human diseases.

The porous polymer material according to the present invention may be used as a biomaterial by including various materials therein because of its unique structure. In this case, the dense pore structure formed in an inner layer of the porous polymer material is preferable in terms of the sustained release of various materials (for example, bioactive molecules, etc.).

The porous polymer material according to the present invention may include at least one kind of biodegradable material selected from the group consisting of poly(ε-caprolactone), polydioxanone, poly(lactic acid), a poly(glycolicacid),poly(lactic acid-co-glycolic acid copolymer, a copolymer of poly(β-hydroxybutyrate) and polyhydroxybutyric acid-cohydroxyvalericacid, poly(γ-ethyl glutamate), a polyanhydride copolymer; a polyethylene oxide-polylactic acid copolymer; a polyethyleneoxidepolylactic-co-glycolic acid copolymer; and a polyethylene oxide-polycaprolactone copolymer, but is not limited thereto. Among the above biodegradable polymers, poly(ε-caprolactone) may be the most preferable to use.

Further, according to anotherexample of the present invention, a hydrophilic polymer may be further included in the preparation of the porous polymer material in order to improve the ease of introduction of bioactive molecules into the porous polymer material.

The hydrophilic polymer may be at least one selected from the group consisting of a polyethylene oxide-polypropylene oxide copolymer, a polyethylene oxide-polylactic acid copolymer, a poly(lactic acid-co-glycolic acid) copolymer, a polyethylene oxide-glycolic acid copolymer, a polyethyleneoxidepolylactic-co-glycolic acid copolymer, apolyethylene oxide-polydioxanone copolymer, and copolymers thereof, but other materials may be used as long as they have hydrophilicity.

The hydrophilic polymer may be preferably contained in an amount of 0.1 to 50% by weight of the total polymer.

According to one example of the present invention, the porous polymer material may be provided as particles or in the form of a sheet. That is, the polymer material may be formed and used as particles having porosity, or the polymer material may be used in the form of a sheet having a porosity prepared by putting the polymer material into a specific mold.

In the case where the porous polymer material according to the present invention is in the form of particles, an average particle diameter thereof may be preferably 10 to 3000 µm. This is because it is preferable in terms of adhesion of cells to the surface of the porous polymer material, diffusion of body fluid into the porous polymer material, induction of new bone formation, and ease of injection through needle.

Hereinafter, according to one example of the present invention, a method of preparing a porous polymer material will be described.

Figure 1:
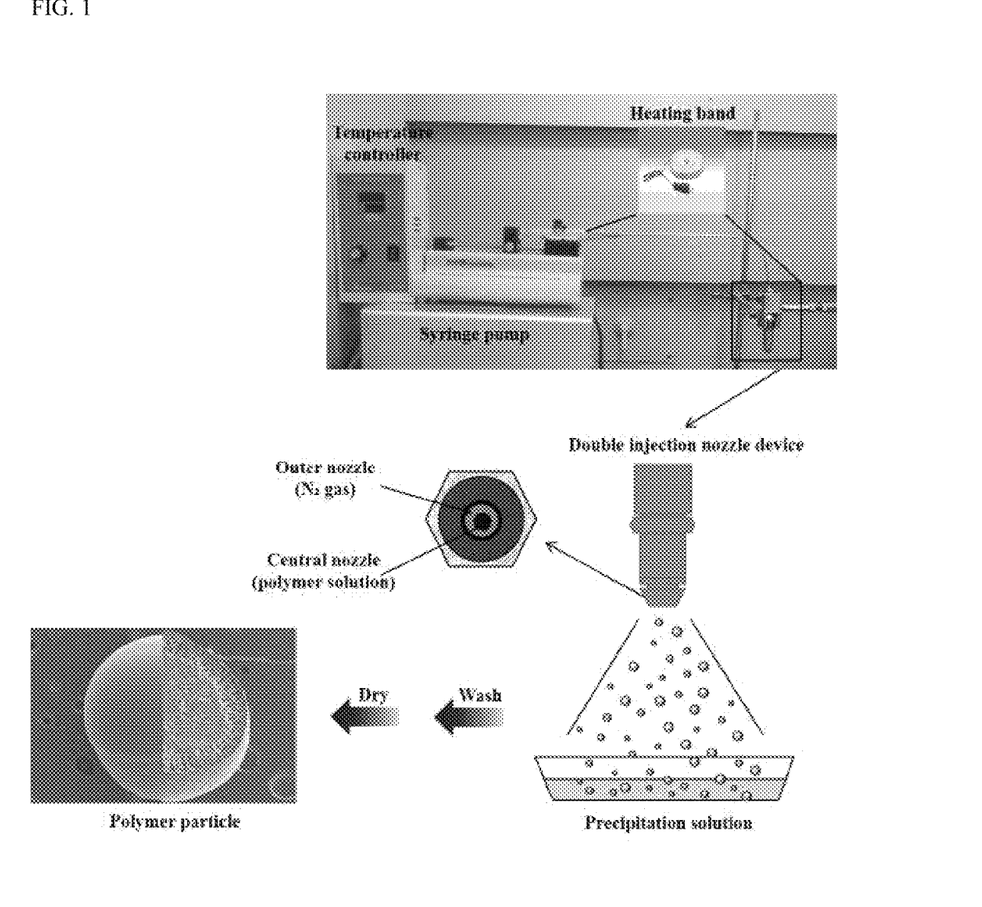
FIG. 1 is a schematic view showing a process of producing a porous poly-ε-caprolactone particle according to the present invention.

First, in the case where a porous polymer material according to the present invention is prepared as particles, the preparation process may include operations of: spaying polymer solution and compressed gas into a non-solvent to precipitate the polymers and washing and drying the precipitated polymer to generate porous polymer particles, and the detailed operations are as shown in FIG. 1.

First, a polymer solution is prepared, the polymer solution and the compressed gas are sprayed into the non-solvent and then the polymer is precipitated in the non-solvent.

In the preparation of the polymer solution, it may be preferable to use at least one kind of solvent selected from the group consisting of tetraglycol, 1-methyl-2-Pyrrolidinone (NMP), triacetin, and benzyl alcohol, which are harmless to a human body. In addition, it may be preferable to dissolve the polymer in the solvent under the condition that the melting point of each polymer used is maintained.

In the present invention, it is possible to prepare the porous polymer material even with a solvent harmless to a human body, without using toxic organic solvent as in the prior art, and the porous polymer material may be applied to a biomaterial requiring a sustained release of loaded bioactive molecules.

In addition, the concentration of the polymer solution according to the present invention may be from 1 to 50% by weight, preferably, from 10 to 20% by weight in the preparation of the porous polymer particles. When the concentration of the polymer solution is less than 1% by weight, there may be problems that the polymer is not precipitated or the physical properties thereof are weakened, and when the concentration of the polymer solution is in excess of 50% by weight, the viscosity of the solution is high and thus it is difficult to dissolve or to handle.

Additionally, according to another example of the present invention, a hydrophilic polymer may be further included in the polymer solution.

The hydrophilic polymer may be at least one kind of polymer selected from the group consisting of a polyethylene oxide-polypropylene oxide copolymer, a polyethylene oxide-polylactic acid copolymer, a poly(lactic acid-co-glycolic acid) copolymer, a polyethylene oxide-glycolic acid copolymer, a polyethyleneoxidepolylactic-co-glycolic acid copolymer, a polyethylene oxide-polydioxanone copolymer, and copolymers thereof, but other materials may be used as long as they have hydrophilicity.

The hydrophilic polymer may be preferably contained in an amount of 0.1 to 50% by weight of the total polymer.

After preparing the polymer solution as described above, the polymer solution is sprayed through a double injection nozzle together with the compressed gas while maintaining the melting point of each polymer, as shown in FIG. 1, to immerse the polymer solution in the non-solvent.

The non-solvent used to immerse the polymer solution may be at least one selected from the group consisting of ethanol, methanol, isopropanol, hexane, and ether, but is not limited thereto.

A period of time for precipitating the polymer solution in the non-solvent may be from 1 minute to 12 hours, and may be appropriately adjusted according to a desired particle size of the porous polymer.

Moreover, in the present invention, it may be preferable to spray the compressed gas as well when the polymer solution is immersed in the non-solvent, in order to immerse the polymer solution in a droplet state in the non-solvent by using the compressed gas. As such, when the compressed gas and the polymer solution are sprayed together, it is possible to produce the porous polymer particles having various particle sizes.

The term "compressed gas" refers to a gas compressed to such a degree that a constant pressure can be applied when the polymer solution is sprayed, and may include, for example, an inert gas, such as a nitrogen gas or an argon gas, or ambient air.

It may be preferable that the compressed gas is sprayed at a rate of 0.1 to 50 L/min to produce porous polymer particles having various particles with average particle sizes ranging from about 10 to 3000 µm.

In addition, it may be preferable to simultaneously spray the compressed gas and the polymer solution using a double injection nozzle device. Here, the "double injection nozzle device" may refer to a device having a nozzle formed on an outer portion thereof to inject the compressed gas and a nozzle formed at the central portion thereof to inject the polymer solution, as shown in FIG. 1.

It may be preferable that the double injection nozzle device injects the polymer solution at a distance of 1 to 50 cm from the non-solvent. This is because the polymer solution can be injected as a spherical form (in a droplet state) into the non-solvent and be precipitated as the particle shape.

As soon as the sprayed polymer solution is immersed in the non-solvent, as shown in FIG. 1, the polymer begins to precipitate at the surface where the polymer solution in the form of particles makes in contact with the non-solvent, a plurality of pores are formed while the solution and the non-solvent are exchanged, and at the same time the formed pores are connected to each other to form a dense structure.

Secondly, the polymer immersed into the non-solvent is washed and dried to form the porous polymer particles. The washing and drying method is not particularly limited and may be performed according to a known method.

Figure 2A:
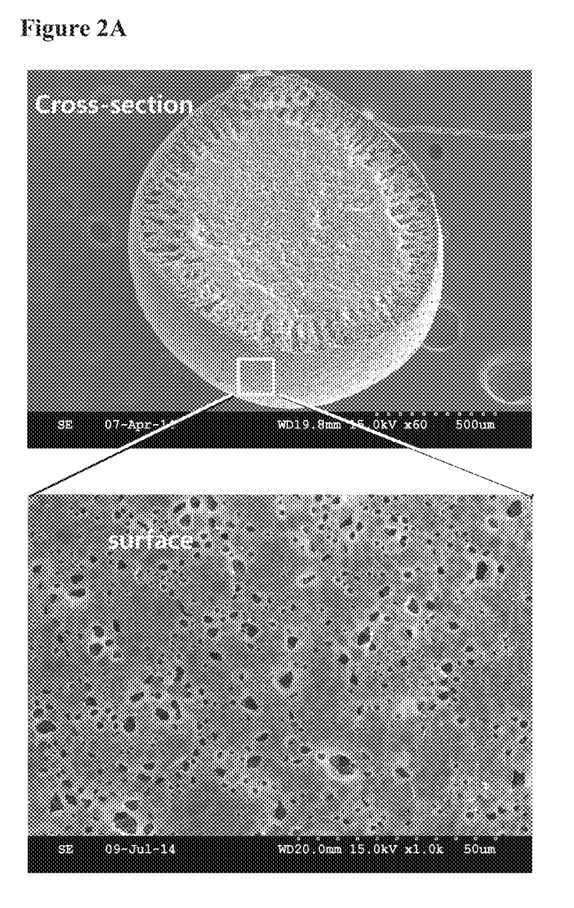
FIGS. 2A-2C are electron-scanning electron microscope (SEM) photographs of a surface and cross-section of the porous poly-ε-caprolactone particle according to Example 1.
Figure 2B:
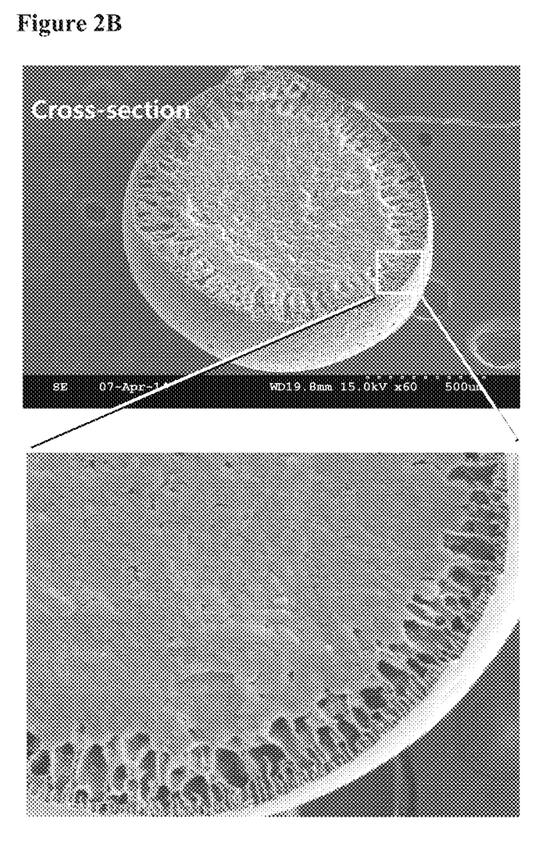
Figure 2C:
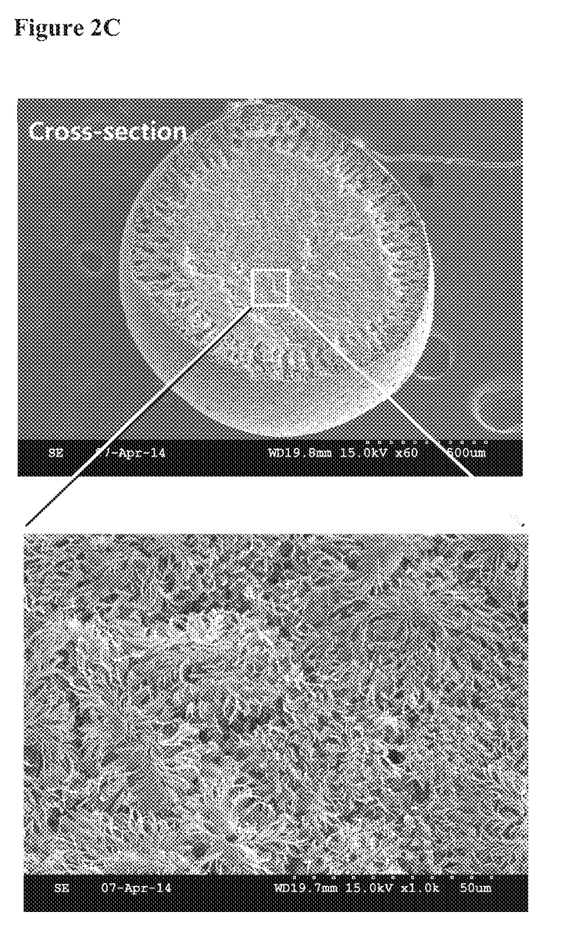

The prepared porous polymer material according to the present invention is in the form of particles. FIG. 2A shows a cross section and an enlarged view of a surface of the porous poly-ε-caprolactone particle according to Example 1, FIG. 2B shows a cross section and an enlarged view of a portion which is disposed between a central portion of cross-section and a surface of the porous poly-ε- caprolactone particle according to Example 1, FIG. 2C shows a cross section and an enlarged view of a central portion of the cross section of the porous poly-ε-caprolactone particle according to Example 1. As depicted in FIG. 2A, FIG. 2B and FIG. 2C, the porous poly-ε-caprolactone particle has not only a porous structure having pores with various sizes on its surface, but also a porous structure in which unique porous structure seemed to be stacked with leaves are densely connected to each other. More specifically, the porous structure includes a plurality of first pores formed over the surface of the poly-ε-caprolactone particle as shown in FIG. 2A, a plurality of second pores in the form of column pores and formed up to a certain distance from the surface of the poly-ε-caprolactone particle as shown FIG. 2B, and a plurality of third pores connected to each other and disposed under the plurality of second pores as shown FIG. 2C.

The porous polymer material according to the present invention prepared through the above processes has a variety of average particle sizes ranging from 10 to 3000 μm. Therefore, according to the particle size, the porous polymer material may be applied to various human implant applications, such as cosmetic filling materials, filling materials for treatment of urinary incontinence, filling materials for treatment of fecal incontinence, filling materials for reconstruction of vocal cords, bone filling materials, and tissue engineering supports.

For example, particles having an average particle size of 100 μm or less among the above porous polymer particles may be applied to a cosmetic filling materials and a tissue engineering support which are intended for tissue regeneration, treatment of urinary/fecal incontinence, and the reconstruction of vocal cords. In addition, particles having an average particle size of 300 μm or greater among the above porous polymer particles may be applied to a bone filling material.

Moreover, when the particles are used for each of the applications, the physical properties required for the purpose should be maintained.

Further, when the porous polymer material is in the form of a sheet, the porous polymer material may be prepared by filling a polymer solution into a mold, immersing polymer solution filled in the mold into a non-solvent, and washing and drying the polymer.

The preparation of the polymer solution may be carried out through the same processes as the porous polymer material in the form of particles.

The prepared polymer solution is filled in the mold having a specific shape. In this case, the mold to be used is not particularly limited, and may be any mold capable of maintaining its shape so as to prepare the porous polymer material in the form of a sheet.

Then, the polymer solution filled in the mold is precipitated in the non-solvent, washed and dried to obtain the porous polymer material in the form of a sheet.

The non-solvent may be the same materials as those used to prepare the polymer material in the form of particles, and the washing and drying method is not particularly limited and may be performed according to a known method.

Similarly to the structure of the porous polymer material in the form of particles described above, the porous polymer material prepared in the form of a sheet has not only a porous surface structure having pores with various sizes, but also a porous internal structure in which unique porous structure seemed to be stacked with leaves are densely connected to each other.

In the present invention, a porous structure may be prepared by a very simple method without surface modification or a specific additive for formation of such a unique porous structure, hence simplifying the process and reducing manufacturing costs.

In addition, the present invention provides a biomaterial using a porous polymer material which has a porous structure over the entire polymer and has a dense porous structure in which pores are connected to each other therein.

Further, bioactive molecules may be loaded into the porous polymer material according to the present invention, and the loaded bioactive molecules may be released from the porous polymer material in a sustained manner.

Conventionally, for the sustained release of bioactive molecules, methods of linking a porous polymer material and bioactive molecules using covalent bonds, heparin, or the like have been used.

However, in the present invention, the sustained release of the bioactive molecules loaded into the porous polymer material is possible only by a unique structure of the porous polymer material itself according to the present invention, without using any additive or the surface modification method on the surface of the porous polymer material for the loading of the bioactive molecules and the sustained release.

The bioactive molecule may be one selected from: at least one kind of peptide/protein selected from the group consisting of cytokine, hormone, insulin, and antibodies; at least one kind of growth factor selected from the group consisting of fibroblast growth factors (FGFs), a vascular endothelial growth factor (VEGF), a nerve growth factor (NGF), a brain-derived neurotrophic factor (BDNF), transforming growth factors (TGFs), bone morphogenetic proteins (BMPs), an epidermal growth factor (EGF), an insulin-like growth factor (IGF), and a platelet-derived growth factor (PDGF); genes; and vaccines.

In the present invention, the bioactive molecules may be loaded into the surface and inside of the porous polymer material.

In a method of loading the bioactive molecules into the porous polymer material, when a positive pressure is applied to a syringe into which an aqueous solution of bioactive molecules prepared at a specific concentration and a porous polymer material are stored, the bioactive molecules are introduced into the surface and inside of the porous polymer material due to the permeation of an aqueous solution containing the bioactive molecules into the porous particle and adsorption to the surface of the polymer material.

In addition, when the porous polymer material into which the bioactive molecules are loaded is used for at least one application of a biomaterial selected from, for example, cosmetic filling materials, filling materials for treatment of urinary incontinence, filling materials for treatment of fecal incontinence, filling materials for reconstruction of vocal cords, bone filling materials, and tissue engineering supports, the bioactive molecules are released from the porous polymer material in a sustained manner.

The sustained release of the bioactive molecules is accomplished by repeating desorption/adsorption of the bioactive molecules on the dense porous structure of the polymer material in which the pores are connected to each other while as the bioactive molecules loaded in the porous polymer material pass through the dense porous structure (allowing of complex release path like 3D maze). Therefore, since the bioactive molecules are repeatedly disrobed and adsorbed while passing through the dense porous structure, the time taken for release from the porous polymer material becomes longer than that of bioactive molecules loaded according to the conventional method.

Such a sustained release characteristic is different from the release characteristic shown in a conventional polymer material having a simple porous structure, which may be attributed to the unique internal structure of the porous polymer material of the present invention.

Hereinafter, examples of the present invention will be described in detail. The following examples are provided to illustrate the present invention, and the scope of the present invention should not be construed as being limited to the examples. In addition, specific compounds are used in the following examples, but it is obvious to those skilled in the art that the equivalents thereof can exhibit the same or similar degrees of effects.

EXAMPLE 1

Preparation of Porous PCL Particles

A biocompatible biodegradable polymer solution was prepared by dissolving poly-ε-caprolactone, which exhibits biocompatibility, in tetraglycol, harmless to a human body, at a weight percent of 15% at a temperature of 90° C.

The prepared polymer solution was transferred into a 10-mL syringe, a tip of the syringe was connected to a stainless needle, and then the needle was attached to a double injection nozzle device. At this time, a heating band was wound around the syringe, the stainless needle, and the double injection nozzle device to maintain the temperature at 90° C. so as to prevent the solution from hardening in the course of spraying. A distance between the end of the injection nozzle device and a surface of a non-solvent was fixed at 20 cm.

The polymer solution was injected into a central portion of a double injection nozzle at a rate of 10 mL/h using a syringe pump, an $N_2$ gas was injected into an outer portion of the double injection nozzle at a constant flow rate of 1 L/min, and the polymer solution and the $N_2$ gas were sprayed into the non-solvent.

As soon as the sprayed polymer solution came in contact with the non-solvent (50% ethanol), polymer began to precipitate on a surface of the polymer solution, and after the first 1 hour of precipitation, the remaining solvent was thoroughly washed with an excess of ultrapure water changed every hour for 6 hours.

Vacuum dry was carried out after the washing, and porous PCL particles with a uniform shape which were separated by size were obtained using a micro sieve.

EXAMPLE 2

Preparation of Porous PCL Sheet

A biocompatible biodegradable polymer solution was prepared by dissolving poly -ε-caprolactone, which exhibits biocompatibility, in tetraglycol, harmless to a human body, at a weight percent of 15% at a temperature of 90° C.

After the polymer solution was cast in a fixed mold (5×5 $cm^2$; thickness of 0.4 mm) stored at room temperature, the mold containing the polymer solution was impregnated with a non-solvent (50% ethanol). As soon as the sprayed polymer solution came in contact with water, polymer began to precipitate on a surface of the polymer solution, and after the first 1 hour of precipitation, the remaining solvent was thoroughly washed with an excess of ultrapure water changed every hour for 6 hours. A porous PCL sheet was prepared by performing vacuum dry after the washing.

EXPERIMENTAL EXAMPLE 1

Confirmation on Structure of Porous PCL Particle

The surface and cross-sectional structures of the porous PCL Particle prepared according to Example 1 were observed through an electron-scanning electron microscope (SEM), and the result is shown in FIG. 2A, FIG. 2B and FIG. 2C.

As shown in FIG. 2A, FIG. 2B and FIG. 2C, the surface of the porous polymer particle prepared according to Example 1 consisted of micro-sized pores.

In addition, in the inside of the particle, it was confirmed that columnar porous structures were formed up to a certain distance from the surface, below the columnar porous structures, a plurality of pores were connected to each other to form bundles and the bundles were connected again to each other in a dense structure.

Further, it was confirmed that the average particle diameter of the prepared particles was 10 to 3000 μm.

EXAMPLE 2

Confirmation on Structure of Porous PCL Sheet

The surface and cross-sectional structures of the porous PCL sheet prepared according to Example 2 were observed through a SEM, and it was confirmed that a sheet surface (outside) had micro-sized pores and in the inside of the sheet, a plurality of pores were connected to each other to form bundles and the bundles were connected again in a dense structure, like in Example 1.

EXAMPLES 3 TO 5

Preparation of Porous PCL/Pluronic F127 Particles

A biocompatible biodegradable polymer solution was prepared by mixing poly-ε-caprolactone, which exhibits biocompatibility, and Pluronic F127, which has biocompatibility and hydrophilicity, to obtain a 5 wt % (based on PCL), a 10 wt % (based on PCL), and a 20 wt % (based on PCL) mixtures, (Examples 3, 4, and 5, respectively), and dissolving the resultant mixture in tetraglycol, which is harmless to a human body, at a weight percent of 15%.

The prepared polymer solution was transferred to a 10-mL syringe, a tip of the syringe was connected to a stainless needle, and then the needle was attached to a double injection nozzle device. At this time, a heating band was wound around the syringe, the stainless needle, and the double injection nozzle device to maintain the temperature at 90° C. so as to prevent the solution from hardening in the course of spraying. A distance between the end of the injection nozzle device and a surface of a non-solvent was fixed at 20 cm.

The polymer solution was injected into a central portion of a double injection nozzle at a rate of 10 mL/h using a syringe pump, an $N_2$ gas was injected into an outer portion of the double injection nozzle at a constant flow rate of 1 L/min, and the polymer solution and the $N_2$ gas were sprayed into the non-solvent.

As soon as the sprayed polymer solution came in contact with the non-solvent (50% ethanol), polymer began to precipitate on a surface of the polymer solution, and after the first 1 hour of precipitation, the remaining solvent was thoroughly washed with an excess of ultrapure water changed every hour for 6 hours.

The washed particles were dried to produce final porous polymer particles.

It was observed that the surface/cross-sectional structures and particle size distribution of the porous PCL/Pluronic F127 particles prepared above were similar to those of Example 1.

EXAMPLES 6 TO 8

Preparation of Porous PCL/Pluronic F127 Sheet

A biocompatible biodegradable polymer solution was prepared by mixing poly-ε-caprolactone, which exhibits biocompatibility, and Pluronic F127, which has biocompatibility and hydrophilicity, to obtain a 5 wt % (based on PCL), a 10 wt % (based on PCL), and a 20 wt % (based on PCL) mixtures, (Examples 6, 7, and 8, respectively), and dissolving the resultant mixture in tetraglycol, which is harmless to a human body, at a weight percent of 15%.

After the polymer solution was cast in a fixed mold (5×5 cm²; thickness of 0.4 mm) stored at room temperature, the mold containing the polymer solution was impregnated with a non-solvent (50% ethanol). As soon as the sprayed polymer solution came in contact with water, polymer began to precipitate on a surface of the polymer solution, and after the first 1 hour of precipitation, the remaining solvent was thoroughly washed with an excess of ultrapure water changed every hour for 6 hours. A porous PCL sheet was prepared by performing vacuum dry after the washing.

It was observed that the surface/cross-sectional structures of the porous PCL/Pluronic F127 sheet prepared above were similar to those of Example 2.

EXAMPLES 9 TO 12

Loading of Bone Morphogenic Protein into Porous PCL Particles and Porous PCL/Pluronic F127 Particles The porous PCL particles according to Example 1 and the porous PCL/Pluronic F127 particles prepared according to Examples 3 to 5, in which poly-ε-caprolactone and Pluronic F127, which has biocompatibility and hydrophilicity, were mixed to obtain a 5 wt %, a 10 wt %, and a 20 wt % mixtures, were placed into a 10-ml syringe containing a bone morphogenic protein 2 (BMP-2) aqueous solution with a concentration of 200 ng/ml (dissolved in PBS containing 1% BSA), a positive pressure was applied to introduce the aqueous solution containing the BMP-2 into the particles, the resultant (positive pressure applied) particles were then stored in a refrigerator for 3 hours, and an excessive amount of the BMP-2 aqueous solution was carefully removed and lyophilized to prepare porous PCL particles loaded with the BMP-2.

EXAMPLES 13 TO 16

Loading of Bone Morphogenic Protein in Porous PCL Sheet and Porous PCL/Pluronic F127 Sheet The porous PCL sheet according to Example 2 and the porous PCL/Pluronic F127 sheet prepared according to Examples 6 to 8, in which poly-ε-caprolactone and Pluronic F127, which has biocompatibility and hydrophilicity, were mixed to obtain a 5 wt %, a 10 wt %, and a 20 wt % mixtures, were placed into a 10-ml syringe containing a BMP-2 aqueous solution with a concentration of 200 ng/ml (dissolved in PBS containing 1% BSA), a positive pressure was applied to introduce the aqueous solution containing the BMP-2 into the sheet, the resultant (positive pressure applied) sheet was then stored in a refrigerator for 3 hours, and an excessive amount of the BMP-2 aqueous solution was carefully removed and lyophilized to produce a porous PCL sheet loaded with BMP-2.

COMPARATIVE EXAMPLE 1

Loading of BMP-2 in Porous PCL Particles into which Heparin was Introduced

BMP-2 was loaded in porous PCL particles into which heparin was introduced using a method described in Korean Patent Application No. 2010-0101637.

EXPERIMENTAL EXAMPLE 3

Figure 3:
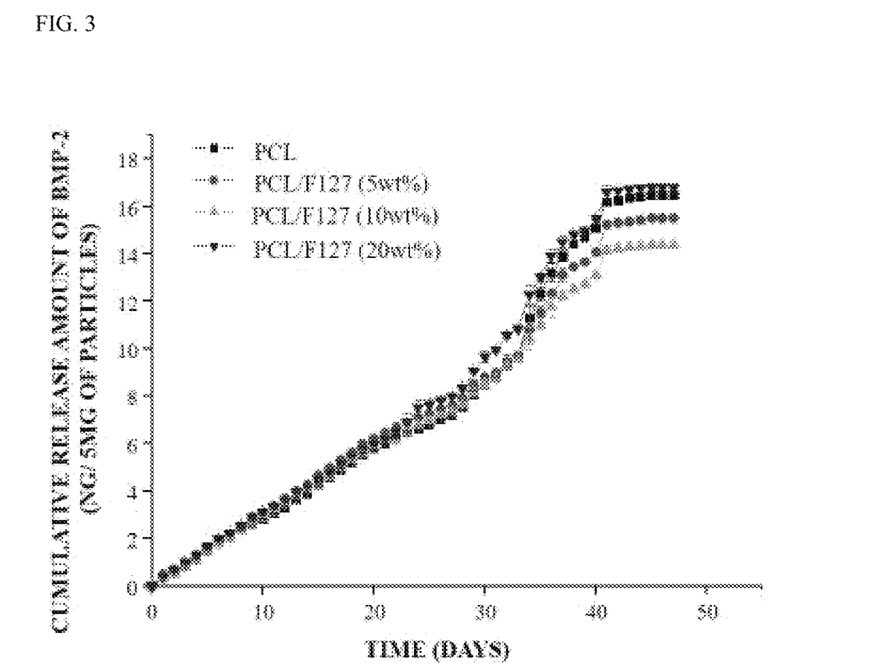
FIG. 3 is a graph showing a release behavior of a bone morphogenetic protein loaded in the porous poly-ε-caprolactone particle.

Confirmation on Release Behavior of BMP-2 from Porous PCL Particles and Porous PCL/Pluronic F127 Particles Release behavior of BMP-2 from each of the porous particles loaded with the BMP-2, which were prepared in Examples 9 to 12, was confirmed, and the results are shown in FIG. 3.

The release behavior was achieved by placing PCL particles loaded with BMP-2under four different conditions (Pluronic F127 at 0, 5, 10, and 20 wt %) in PBS containing 1% BSA, respectively, whereby the BMP-2 was released to the solution. Protein was collected and quantitated every other day by sandwich ELISA.

As shown in the results in FIG. 3, it was observed that the protein was slowly released over time regardless of the content of Pluronic F127. In particular, it was confirmed that the BMP was slowly released for about 50 days.

EXPERIMENTAL EXAMPLE 4

Confirmation on Release Behavior of BMP-2 from Porous PCL Sheet and Porous PCL/Pluronic F127 Sheet Release behavior of BMP-2 from each of the porous sheets loaded with the BMP-2, which were prepared in Examples 13 to 16, was confirmed in the same manner as Experimental Example 3, and results of the release behavior were confirmed to be similar to those of the porous PCL particles.

COMPARATIVE EXAMPLE 1

Confirmation on Release Behavior of BMP-2 from Porous PCL Particles into which Heparin was Introduced Release behavior of BMP-2 from the porous particles loaded with BMP-2, which were prepared in Comparative Example 1, was confirmed in the same manner as Experimental Example 3. As expected, BMP-2 was released in a sustained manner over about 28 days, confirming that the sustained release was possible by ionic interaction between heparin and BMP-2.

Through a comparison between Experimental Example 3 and Comparative Example 1, it was confirmed that, without using any additive and chemical modification method, bioactive molecules loaded on the porous polymer material prepared according to the present invention induced release of the bioactive molecules for a longer period than when bioactive molecules were loaded using existing heparin as a surface modification method.

EXAMPLE 17

Loading of Trail into Porous PCL Particles

The porous PCL particles according to Example 1 were placed into a 10-ml syringe containing an aqueous solution of TNF-related apoptosis-inducing ligand (TRAIL) with a concentration of 1000 ng/ml (in DMEM), a positive pressure was applied to introduce an aqueous solution containing TRAIL into the particles, the resultant (positive pressure applied) particles were then stored in a refrigerator for 3 hours, and an excessive amount of the aqueous solution of TRAIL was carefully removed and lyophilized to produce porous PCL particles loaded with TRAIL.

EXPERIMENTAL EXAMPLE 4

Confirmation on Release Behavior of Trail from Porous PCL Particles

Release behavior of TRAIL from each of the porous PCL particles loaded with TRAIL, which were prepared in Example 17, was confirmed.

It was confirmed that TRAIL was slowly released from the porous PCL particles loaded with TRAIL over time, and the TRAIL was released in a sustained manner over about 50 days.

EXAMPLE 18

Loading of Vaccine into Porous PCL Particles

The porous PCL particles according to Example 1 were placed into a 10-mL syringe containing an aqueous solution of pancreatic cancer vaccine with a concentration of 1000 ng/ml (in DMEM), a positive pressure was applied to introduce the aqueous solution containing the vaccine into the particles, the resultant (positive pressure applied) particles was then stored in a refrigerator for 3 hours, and an excessive amount of the aqueous solution of vaccine was carefully removed and lyophilized to produce a porous PCL particles loaded with vaccine.

EXPERIMENTAL EXAMPLE 5

Confirmation on Release Behavior of Vaccine from Porous PCL Particles

Release behavior of vaccine from each of the porous PCL particles loaded with the vaccine, which were prepared in Example 18, was confirmed.

The vaccine was released slowly from the porous PCL particles loaded with vaccine over time, and it was confirmed that the vaccine was released in a sustained manner over about 50 days.

The invention claimed is:

1. A porous polymer material having a porous structure over a surface and an inside of the polymer material,
wherein the porous structure includes a plurality of first pores formed over the surface of the polymer material, a plurality of second pores in the form of column pores and formed up to a certain distance from the surface of the polymer material, and a plurality of third pores connected to each other and disposed under the plurality of second pores,
wherein the porous polymer material may be in the form of particles, and an average particle size of the particles is 10 to 3000 μm.

2. The porous polymer material of claim 1, wherein the porous polymer is at least one selected from the group consisting of poly(ε-caprolactone), polydioxanone, poly(lactic acid), poly(glycolicacid), a poly(lactic acid-co-glycolic acid) copolymer, a copolymer of poly((β-hydroxybutyrate) and polyhydroxybutyric acid-cohydroxyvalericacid, poly(γ-ethyl glutamate), a polyanhydride copolymer, a polyethylene oxide-polylactic acid copolymer, a polyethyleneoxidepolylactic-co-glycolic acid copolymer, and a polyethylene oxide-polycaprolactone copolymer.

3. The porous polymer material of claim 1, wherein the porous polymer material further includes hydrophilic polymer, wherein the hydrophilic polymer is at least one selected from the group consisting of a polyethylene oxide-polypropylene oxide copolymer, a polyethylene oxide-polylactic acid copolymer, a poly(lactic acid-co-glycolic acid) copolymer, a polyethylene oxide-glycolic acid copolymer, a polyethyleneoxidepolylactic-co-glycolic acid copolymer, a polyethylene oxide-polydioxanone copolymer, and copolymers thereof.

4. A biomaterial using a porous polymer material that has a porous structure, the porous structure includes a plurality of first pores formed over the surface of the polymer material, a plurality of second pores in the form of column pores and formed up to a certain distance from the surface of the polymer material, and a plurality of third pores connected to each other and disposed under the plurality of second pores, wherein the porous polymer material may be in the form of particles and an average particle size of the particles is 10 to 3000 μm,
wherein bioactive molecules are loaded in the surface and an inside of the porous polymer material, and the loaded bioactive molecules are released from the porous polymer material in a sustained manner.

5. The biomaterial of claim 4, wherein a sustained release of the bioactive molecules is accomplished by repeating desorption/adsorption of the bioactive molecules on the porous structure of the polymer material in which the pores are connected to each other while the bioactive molecules loaded in the porous polymer material pass through the porous structure.

6. The biomaterial of claim 4, wherein the bioactive molecule is at least one selected from: at least one kind of peptide-protein selected from the group consisting of cytokine, hormone, insulin, and antibodies;
at least one kind of growth factor selected from the group consisting of fibroblast growth factors (FGFs), a vascular endothelial growth factor (VEGF), a nerve growth factor (NGF), a brain-derived neurotrophic factor (BDNF), transforming growth factors (TGFs), bone morphogenetic proteins (BMPs), an epidermal growth factor (EGF), an insulin-like growth factor (IGF), and a platelet-derived growth factor (PDGF); genes; and vaccines.

7. The biomaterial of claim 4, wherein the biomaterial is being at least one selected from cosmetic filling materials, filling materials for treatment of urinary incontinence, filling materials for treatment of fecal incontinence, filling materials for reconstruction of vocal cords, bone filling materials, and tissue engineering supports.

* * * * *